United States Patent [19]

Yasui et al.

[11] Patent Number: 5,021,347

[45] Date of Patent: Jun. 4, 1991

[54] RECOMBINANT VACCINIA VIRUS EXPRESSING E-PROTEIN OF JAPANESE ENCEPHALITIS VIRUS

[75] Inventors: Kotaro Yasui, Tokyo; Asato Kojima, Kuki; Atsushi Yasuda; Takanori Sato, both of Kamakura, all of Japan

[73] Assignees: Nippon Zeon Co., Ltd.; Director-General of National Institute of Health; Tokyo Metropolitan Institute for Neuroscience, all of Tokyo, Japan

[21] Appl. No.: 244,778

[22] Filed: Sep. 15, 1988

[30] Foreign Application Priority Data

Sep. 16, 1987 [JP] Japan .................. 62-231496

[51] Int. Cl.⁵ .............................. C12N 7/01
[52] U.S. Cl. ........................... 435/235; 424/89
[58] Field of Search ............ 435/235, 172.3, 68, 435/70; 424/88, 89; 536/27

[56] References Cited

U.S. PATENT DOCUMENTS

| | | | |
|---|---|---|---|
| 4,603,112 | 7/1986 | Paolletti | 435/235 |
| 4,659,569 | 4/1987 | Mitsuhashi | 424/89 |
| 4,810,492 | 3/1989 | Fujita | 424/88 |

FOREIGN PATENT DOCUMENTS

| | | |
|---|---|---|
| 0110385 | 6/1984 | European Pat. Off. . |
| 62-44178 | 2/1987 | Japan . |
| WO88/03032 | 5/1988 | PCT Int'l Appl. . |
| 2191201 | 12/1987 | United Kingdom . |

OTHER PUBLICATIONS

Mason, P. W. et al., Jun. 1987, *Virology*, 158(2), 361–372.
Sumiyoshi, H. et al., Dec. 1987, *Virology*, 161(2), 497–510.
Sumiyoshi, H. et al., 1986, *Gene*, 48:195–201.
McAda, P. C. et al., Jun. 1987, *Virology*, 158(2), 348–360.
Chemical Abstracts, 107:205157f, (1987).
Sumiyoshi et al., Gene, vol. 48, pp. 195–201, (1986).

*Primary Examiner*—Richard A. Schwartz
*Attorney, Agent, or Firm*—Birch, Stewart, Kolasch & Birch

[57] ABSTRACT

There is provided a recombinant vaccinia virus having inserted cDNA coding for E-protein of Japanese encephalitis virus into a genome region non-essential to growth of a vaccinia virus, in the form of capable expression. The recombinant vaccinia virus is useful as a live vaccine.

8 Claims, 9 Drawing Sheets

FIG. 1

JAPANESE ENCEPHALITIS VIRUS GENOME RNA (11Kbase)

(1) 5'▭3' + ATP

↓ POLY(A) POLYMERASE (2) 5'▭3' POLY(A) TAIL
　　　　　AAAAAAA
　　　　　　TTTTT
　　+d(A·G·C·T)TP　OLIGO dT PRIMER
　　REVERSE
　　TRANSCRIPTASE

↓

(3) ▭ AAAA
　　▨ TTTT

↓ E.coli RNaseH
　 E.coli DNA POLYMERASE　+d(A·G·C·T)TP pUC9

(4) ▨▨ DOUBLE STRANDED cDNA

DIGESTION WITH Pst I
　　　　　　　　　　　　　　　TERMINAL TRANSFERASE
　　　　　　　　　　　　　　　+dGTP
　　TERMINAL TRANSFERASE + dCTP
　　　　　　　　　　　　　　　　GGG
(5) CCCC ▨▨ CCCC　　　　　　　GGG pUC9

↓ LIGATION (6) ⬭　　SEQUENTIAL ANALYSIS OF ▬ PORTION

JAPANESE ENCEPHALITIS GENOME RNA

(7) 5'▭3'

↓ SYNTHETIC OLIGONUCLEOTIDE (20-mer) PRIMER
　 +d(A·G·C·T)TP
　 REVERSE TRANSCRIPTASE

5'▭3'
▨■

↓ E.coli RNaseH
　 E.coli DNA POLYMERASE +d(A·G·C·T)TP

SUBSEQUENTLY, OPERATIONS OF (4) AND (5) ARE PERFORMED TO LIGATE cDNA WITH pUC9.

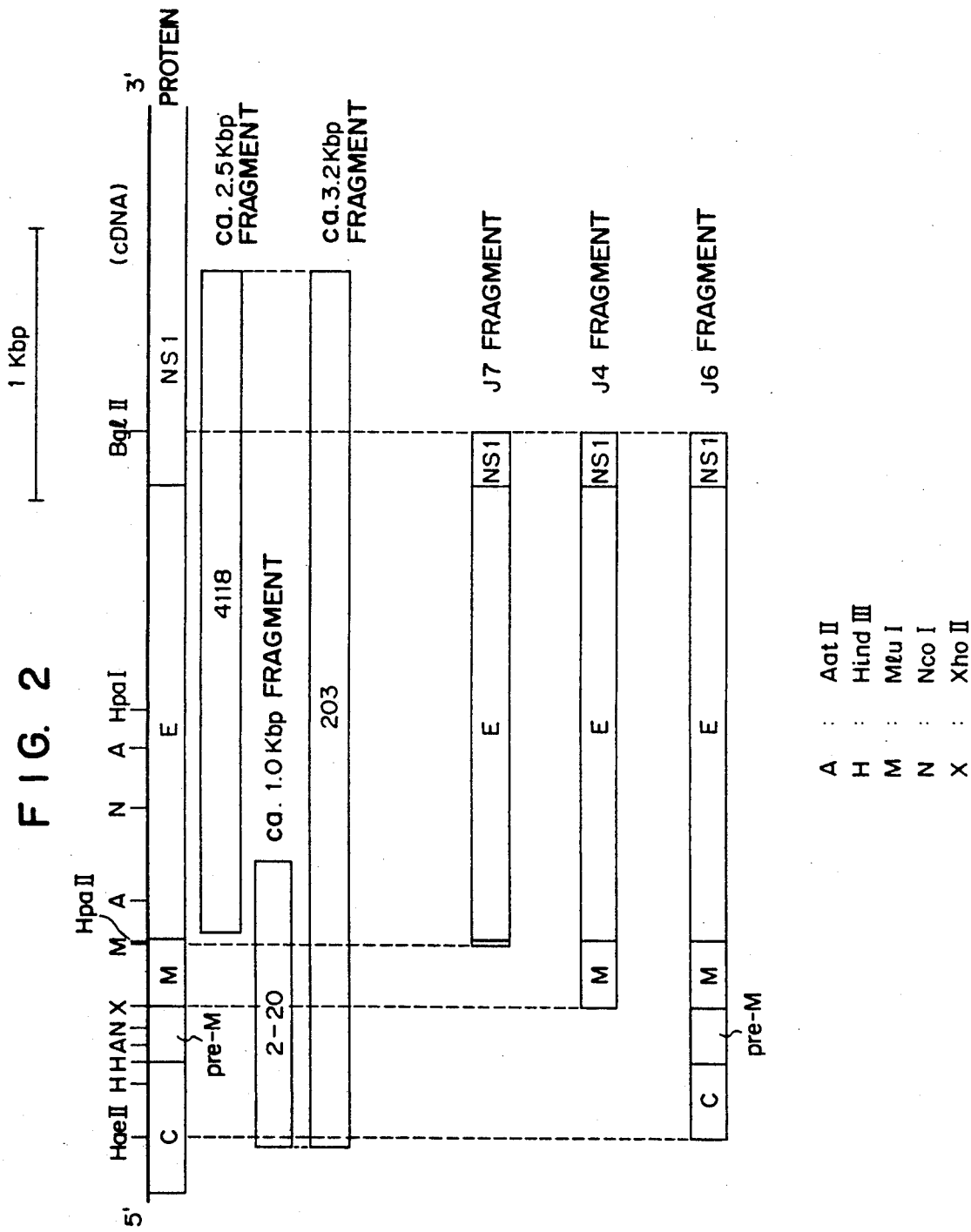

FIG. 3A

```
        -244  2-20                                                                                                                                                                  Hae II
        ATC ACG TTC TTC AAG TTT ACA GCA TTA GCC CCG ACC AAG GCG CTT TTA GGC CGA   -227
        Ile Thr Phe Phe Lys Phe Thr Ala Leu Ala Pro Thr Lys Ala Leu Leu Gly Arg

TGG AAA GCA GTG GAA AAG AGT GTG GCA ATG GTG GCA ATG CAT CTT ACT AGT TTC AAA CGA   -209
        Trp Lys Ala Val Glu Lys Ser Val Ala MET Lys His Leu Thr Ser Phe Lys Arg

GAA CTT GGA ACA CTC ATT GAC GCC GTG AAC AAG CGG AGA AAA CAA AAC AAA   -191
        Glu Leu Gly Thr Leu Ile Asp Ala Val Asn Lys Arg Arg Lys Gln Asn Lys

AGA GGA GAA AAT GAA GGC TCA ATC ATG TGG CTC GCA AGC TTG GCA GTT GTC ATA   -173
        Arg Gly Gly Asn Glu Gly Ser Ile MET Trp Leu Ala Ser Leu Ala Val Ile
                                   ↑ PreM
                                -167 ↑ MET
        GCT TAC GCA GGA GCA ATT GCA GAC ATT CCC ACC TCA AAA GGA GCG   -137
        Ala Tyr Ala Gly Ala Ile Ala Asp Val Leu Pro Thr Ser Lys Gly Ala

ATC AAC AAC ACG GAC ATT GCA GAC GTT ATC CTG ATT CCC ACC TCA AAA GGA GCG   -137
        Ile Asn Asn Thr Asp Ile Ala Asp Val Ile Leu Ile Pro Thr Ser Lys Gly Ala

AAC ATA TGC TGG GTC CGG GCA ATA ATC GAC GTC GGC TAC ATG TGT GAG GAC ACT ATC   -119
        Asn Ile Cys Trp Val Arg Ala Ile Ile Asp Val Gly Tyr MET Cys Glu Asp Thr Ile

ACG TAC GAA TGT CCT AAG TTC ACC ATG GGC AAT GAT CCA GAG GAT GTG GAT TGT   -101
        Thr Tyr Glu Cys Pro Lys Phe Thr MET Gly Asn Asp Pro Glu Asp Val Asp Cys

CGG TGT GAC AAC CAA GAA GTC TAC GTC TAT GGA CGG TGC ACG CGG ACC AGG   -83
        Arg Cys Asp Asn Gln Glu Val Tyr Val Tyr Gly Arg Cys Thr Arg

CAT TCC AAG CGA AGC AGG AGG TCG GTC CAA ACA CAT GGG GAG AGT TCA   -65
        His Ser Lys Arg Ser Arg Arg Ser Val Gln Thr His Gly Glu Ser Ser
                         Xho I ↑ AGA TCC
                                m
```

FIG. 3B

```
      CTA GTG AAT AAA AAA GAG GCT TGG CTG GAT TCA ACG AAA GCC ACA CGG TAT CTC  -47
      Leu Val Asn Lys Lys Glu Ala Trp Leu Asp Ser Thr Lys Ala Thr Arg Tyr Leu

ATG AAA ACT GAG AAC TGG ATC ATA AGG AAT CCT GGC TAT GCT TCT CTG GCG GCG  -29
      MET Lys Thr Glu Asn Trp Ile Ile Arg Asn Pro Gly Tyr Ala Ser Leu Ala Ala

GTA CTT GGC TGG ATG CTT GGC AGT AAC AAC GGT CAA CGC GTG GTA TTT ACC ATC  -11
      Val Leu Gly Trp MET Leu Gly Ser Asn Asn Gly Gln Arg Val Val Phe Thr Ile
                                                                    ▲ 4118
                        Hpall          -1  +1                                +8
      CTC CTG CTG TTG GTC GCT TAC AGT TTT AAT TGT CTG GGA ATG GGC AAT
      Leu Leu Leu Leu Val Ala Pro Ala Tyr Ser Phe Asn Cys Leu Gly MET Gly Asn
                        E CGT GAC TTC ATA GAA GGA GCC AGT GGA GCC ACT TGG GTG GAC TTG GTG CTA GAA  +26
      Arg Asp Phe Ile Glu Gly Ala Ser Gly Ala Thr Trp Val Asp Leu Val Leu Glu Aatll              +44
      GGA GAT AGC TGC TTG ACA ATC ATG GCA AAC GAC AAA CCA ACA TTG GAC GTC CGC
      Gly Asp Ser Cys Leu Thr Ile MET Ala Asn Asp Lys Pro Thr Leu Asp Val Arg ATG ATT AAC ATC GAA GCT AGC CAA CTT GCT GAG GTC AGA AGT TAC TGC TAT CAT  +62
      MET Ile Asn Ile Glu Ala Ser Gln Leu Ala Glu Val Arg Ser Tyr Cys Tyr His GCT TCA GTC ACT GAC ATC ACG ACG GTG GCT CGG AGC CCC ACG ACT GGA GAA GCC  +80
      Ala Ser Val Thr Asp Ile Thr Thr Val Ala Arg Ser Pro Thr Thr Gly Glu Ala CAC AAC GAG AAG CGA GCT GAT AGT AGC TAT GTG TGC AAA CAA GGC TTC ACT GAT  +98
      His Asn Glu Lys Arg Ala Asp Ser Ser Tyr Val Cys Lys Gln Gly Phe Thr Asp
                                                                    2-20  ◄ +116
      CGT GGG TGG GGC AAC GGA CTT TTC GGG AAG GGA AGC ATT GAC ACA TGT
      Arg Gly Trp Gly Asn Gly Leu Phe Gly Lys Gly Ser Ile Asp Thr Cys
```

FIG. 3C

```
                                                                              +134
GCA AAA TTC TCC TGC ACC AGC AAA GCG ATT GGA AGA ACA ATC CAG CCA GAA AAC
Ala Lys Phe Ser Cys Thr Ser Lys Ala Ile Gly Arg Thr Ile Gln Pro Glu Asn
                                                                              +152
ATC AAA TAC GAA GTT GGC ATT TTT GTG CAT GGA ACC ACT TCG GAA AAC CAT
Ile Lys Tyr Glu Val Gly Ile Phe Val His Gly Thr Thr Ser Glu Asn His
                                                                              +170
GGG AAT TAT TCA GCG CAA GTT GGG GCG TCC CAG GCG GCA AAG TTC ACA GTA ACA
Gly Asn Tyr Ser Ala Gln Val Gly Ala Ser Gln Ala Ala Lys Phe Thr Val Thr
                                                                              +188
CCC AAT GCT CCT TCG ATA ACC CTC AAA CTT GGT GAC TAC GGA GAA GTC ACG CTG
Pro Asn Ala Pro Ser Ile Thr Leu Lys Leu Gly Asp Tyr Gly Glu Val Thr Leu
                                                                              +206
GAC TGT GAG CCA AGG AGT GGA CTG AAC ACT GAA GCG TTT TAC GTC ATG ACC GTG
Asp Cys Glu Pro Arg Ser Gly Leu Asn Thr Glu Ala Phe Tyr Val MET Thr Val
                                                                              +224
GGG TCA AAG TCA TTT CTG GTC CAT AGG GAA TGG TTT CAT GAC CTC GCT CTC CCC
Gly Ser Lys Ser Phe Leu Val His Arg Glu Trp Phe His Asp Leu Ala Leu Pro
                                                                              +242
TGG ACG TCC CCT TCG AGC ACA AAC CAG TCC GCT GTT GCT CTC ATG GAA TTT
Trp Thr Ser Pro Ser Ser Thr Ala Trp Arg Ala Ser Ala Val Ala Leu MET Glu Phe
                                                                              +260
GAA GAG GCG CAC GCC ACA AAA CAG GGA GCC ATC GTG GTG CTT GGG TCA CAG GAA GGA
Glu Glu Ala His Ala Thr Lys Gln Gly Ala Ile Val Val Leu Gly Ser Gln Glu Gly
                                                                              +278
GGC CTC CAT CAG GCG TTG GCA GGA GCC TTG GCA GAG TAC AGC TCA GTG
Gly Leu His Gln Ala Leu Ala Gly Ala Leu Val Glu Tyr Ser Ser Val
                                                                              +296
     Hpa I
AAG TTA ACA TCA GGC CAC CTG AAA TGT CTG AAA ATG GAC CCC CTG AAG TTG
Lys Leu Thr Ser Gly His Leu Lys Cys Arg Leu Lys MET Asp Pro Leu Lys Leu
```

FIG. 3D

```
AAA GGC ACT ACG TAC GGC ATG TGT ACA GAA AAA TTC TCG TTC GCG AAA AAT TCG  +314
Lys Gly Thr Thr Tyr Gly MET Cys Thr Glu Lys Phe Ser Phe Ala Lys Asn Ser

GCA GAC ACT GGC CAC GGA ACA GTC ATT GAA CTA TCC TAC TCT GGG AGT GAT      +332
Ala Asp Thr Gly His Gly Thr Val Ile Glu Leu Ser Tyr Ser Gly Ser Asp

GGC CCC TGC AAA ATT CCA ATT GTC TCC GTT GCG AGC CTC AAT GAC ATG ACC CTG  +350
Gly Pro Cys Lys Ile Pro Ile Val Ser Val Ala Ser Leu Asn Asp MET Thr Leu

GTT GGC CGG CTG GTG ACA GTG AAC CCT TTC TGC GCG ACT TCC AGT GCC AAC TCA  +368
Val Gly Arg Leu Val Thr Val Asn Pro Phe Cys Ala Thr Ser Ser Ala Asn Ser

AAG GTG CTG GTC GAG ATG GAA CCC CCC TTC GGA GAC TCC TAC ATC GTG GTT GGA  +386
Lys Val Leu Val Glu MET Glu Pro Pro Phe Gly Asp Ser Tyr Ile Val Val Gly

TGG GGA GAC AAG CAG ATC AAC CAC CAT TGG CAC AAA GCT GGA AGC AGC GCT AGC  +404
Trp Gly Asp Lys Gln Ile Asn His His Trp His Lys Ala Gly Ser Ser Ala Ser

AAG GCC TTT TCA ACA ACT TTG AAG GGA GCT CAA AGA CTG GCA GCG TTG GGC GAC  +422
Lys Ala Phe Ser Thr Thr Leu Lys Gly Ala Gln Arg Leu Ala Ala Leu Gly Asp

ACA GCC TGG GAC TTT GGC TCC ATT GGG GTC TTC AAC ACA CTC TTT AAC ATA GGA AAA GCC  +440
Thr Ala Trp Asp Phe Gly Ser Ile Gly Val Phe Asn Thr Leu Phe Asn Ile Gly Lys Ala

GTT CAC CAA GTG TTT GGT GGT GCC TTC AGA ACA CTC CTC TGG ATG GGA ATG TCT TGG      +458
Val His Gln Val Phe Gly Gly Ala Phe Arg Thr Leu Leu Trp MET Gly MET Ser Trp

ATC ACA CAA GGG CTA ATG GGT GCC CTA CTC ATG GGT GTC AAC GCA CGA            +476
Ile Thr Gln Gly Leu MET Gly Ala Leu Leu MET Gly Val Asn Ala Arg
```

FIG. 3E

```
     GAC CGA TCA ATT GCT TTG GCC TTC TTA GCC ACA GGA GGT GTG CTC GTG TTC TTA  +494
     Asp Arg Ser Ile Ala Leu Ala Phe Leu Ala Thr Gly Gly Val Leu Val Phe Leu

↓+500
     GCG ACC AAT GTG CAT GCT GAC ACT GGA TGT GCC TTT GAC ATC ACA AGA AAA GAG  +512
     Ala Thr Asn Val His Ala Asp Thr Gly Cys Ala Phe Asp Ile Thr Arg Lys Glu

ATG AGA TGT GGA AGT GGC ATC TTT GTG CAC AAC GAC GTG GAA GCC TGG GTG GAC  +530
     MET Arg Cys Gly Ser Gly Ile Phe Val His Asn Asp Val Glu Ala Trp Val Asp

AGG TAT AAA TAC TTG CCA GAA ACG CCC AGA TCC CTA GCG AAG ATC GTC CAC AAA  +548
     Arg Tyr Lys Tyr Leu Pro Glu Thr Pro Arg Ser Leu Ala Lys Ile Val His Lys

BglII
     GCG CAC AAG GAA GGC GTG TGC GGA GTC AGA TCT GTC ACT AGA TTG GAG CAC CAA  +566
     Ala His Lys Glu Gly Val Cys Gly Val Arg Ser Val Thr Arg Leu Glu His Gln

ATG TGG GAA GCC GTA CGG GAC GAA TTG AAC GTC CTG CTC AAA GAG AAT GCA GTG  +584
     MET Trp Glu Ala Val Arg Asp Glu Leu Asn Val Leu Leu Lys Glu Asn Ala Val

GAC CTC AGT GTG GTT GTG AAC AAG CCC GTG GGA AGA TAT CGC TCA GCC CCT AAA  +602
     Asp Leu Ser Val Val Val Asn Lys Pro Val Gly Arg Tyr Arg Ser Ala Pro Lys
```

FIG. 3F

```
CGC CTA TCC ATG ACG CAA GAG AAG TTT GAA ATG GGC TGG AAA GCA TGG GGG AAA   +620
Arg Leu Ser MET Thr Gln Glu Lys Phe Glu MET Gly Trp Lys Ala Trp Gly Lys

AGC ATT CTC TTT GCC CCG GAA TTG GCT AAC TCC ACA TTT GTC GTA GAT GGA CCT   +638
Ser Ile Leu Phe Ala Pro Glu Leu Ala Asn Ser Thr Phe Val Val Asp Gly Pro

GAG ACA AAG GAA TGC CCT GAT GAG AAT AGA GCT TGG AAC AGC ATG CAA ATC GAA   +656
Glu Thr Lys Glu Cys Pro Asp Glu Asn Arg Ala Trp Asn Ser MET Gln Ile Glu

GAC TTC GGC TTT GGC ATC ACA ACC CGT GTG TGG CTG AAA ATT AGA GAG GAG       +674
Asp Phe Gly Phe Gly Ile Thr Thr Arg Val Trp Leu Lys Ile Arg Glu Glu

AGC ACT GAC GAG TGT GAT GGA GCG ATC ATA GGC ACG GCT GTC AAA GGA CAT GTG   +692
Ser Thr Asp Glu Cys Asp Gly Ala Ile Ile Gly Thr Ala Val Lys Gly His Val

GCA GTC CAT AGT GAC TTG TCG TAC TGG ATT GAG AGT CGC TAC AAC GAC ACA TGG   +710
Ala Val His Ser Asp Leu Ser Tyr Trp Ile Glu Ser Arg Tyr Asn Asp Thr Trp

Ball +726
AAA CTT GAG AGG GCA GTC TTT GGA GAG GTC AAA TCT TGC ACT        TGG CCA
Lys Leu Glu Arg Ala Val Phe Gly Glu Val Lys Ser Cys Thr        Trp Pro
```

5,021,347

RECOMBINANT VACCINIA VIRUS EXPRESSING E-PROTEIN OF JAPANESE ENCEPHALITIS VIRUS

FIELD OF THE INVENTION AND RELATED ART STATEMENT

1. Field of the Invention

The present invention relates to a recombinant vaccinia virus and more particularly, to a recombinant vaccinia virus in which cDNA coding for surface antigen protein of Japanese encephalitis virus is inserted in a genome DNA region non-essential to growth of a vaccinia virus.

2. Discussion of Prior Art

As a vaccine against Japanese encephalitis, there has been hitherto used a vaccine containing an inactivated Japanese encephalitis virus as an effective ingredient. A Japanese encephalitis virus strain of Nakayama Health Institute is inoculated in the brain of normal mice and the brain is aseptically collected from mice suffering from Japanese encephalitis, purified by an alcohol-protamine method and inactivated to obtain an undiluted solution of Japanese encephalitis virus vaccine ["Japanese Vaccine" edited by National Institute of Health, revised second edition (published by Maruzen Publishing Co., Ltd., on Jan. 20, 1977)]. This inactivated vaccine encounters shortcomings that a relatively long period of time is required for immunization and a duration period for the immunity is short, although its safety is high.

An attempt has also been made to express a surface antigen protein (hereafter sometimes referred to as E-protein) of Japanese encephalitis virus by genetic manipulation using yeast as a host (Preliminary Agenda for the 34th Meeting of the Japanese Virological Society, page 91, October in 1986) but there is no successful example for production of E-protein in substance. Even if the production were successful, E-protein could not be a live vaccine expected to have immune duration over a long period of time.

In recent years, there has been developed a method for constructing a recombinant vaccinia virus inserted heterogenous DNA therein and there has been proposed a method using, as live vaccine, a recombinant vaccinia virus constructed by insertion of, for example, DNA coding for infectious disease pathogen antigen as heterogenous DNA (for example, Japanese Patent Application KOKAI (Laid-Open) No. 129971/83, Japanese Patent Application KOHYO (Disclosure) No. 500518/85, Patent Application KOHYO (Disclosure) No. 501957/86, etc.).

However, Japanese encephalitis virus belonging to the family Togavirus, the genus Flavivirus has single strand RNA as a genome (body bearing genetic information of virus) and is characterized in that a single polypeptide monocistronically translated from a genome in virus-infected cells is processed (which is used to mean that a single polypeptide is cleaved by protease in cells to form each protein) into a core protein, a matrix protein, E-protein and 5 non-constituent proteins. Therefore, it is difficult in manipulation to insert E-protein-coding cDNA into a vaccinia virus and express the same. Therefore, there is no report on the expression so far.

SUMMARY OF THE INVENTION

Under such circumstances, the present inventors have made extensive investigations, aiming at construction of recombinant vaccinia viruses capable of expressing Japanese encephalitis virus E-protein. As a result, it has been found that by selecting a region encoding E-protein from cDNAs constructed using genome RNA of Japanese encephalitis virus as a template, imparting a translation initiation codon and a translation termination codon to after and before the region, ligating with a promoter of vaccinia virus and inserting the same into a genome DNA region non-essential to growth of the vaccinia virus, a recombinant vaccinia virus capable of expressing Japanese encephalitis virus E-protein in infected cells can be obtained. Thus, the present invention has been accomplished.

According to the present invention, there is provided a recombinant vaccinia virus having inserted cDNA coding for Japanese encephalitis virus E-protein into a genome DNA region non-essential to growth of the vaccinia virus, preferably together with DNA having a promoter function and a translation initiation codon and a translation termination codon artificially added, in a manner capable of allowing expression of the desired protein.

BRIEF DESCRIPTION OF THE DRAWINGS

FIG. 1 indicates procedures for cloning cDNA of Japanese encephalitis virus. FIG. 2 shows positional relationship in restriction enzyme site of cDNA. FIG. 3 shows a base sequence and amino acid sequence of cDNA containing a region coding for E-protein.

DETAILED DESCRIPTION OF PREFERRED EMBODIMENTS

Figure 4:
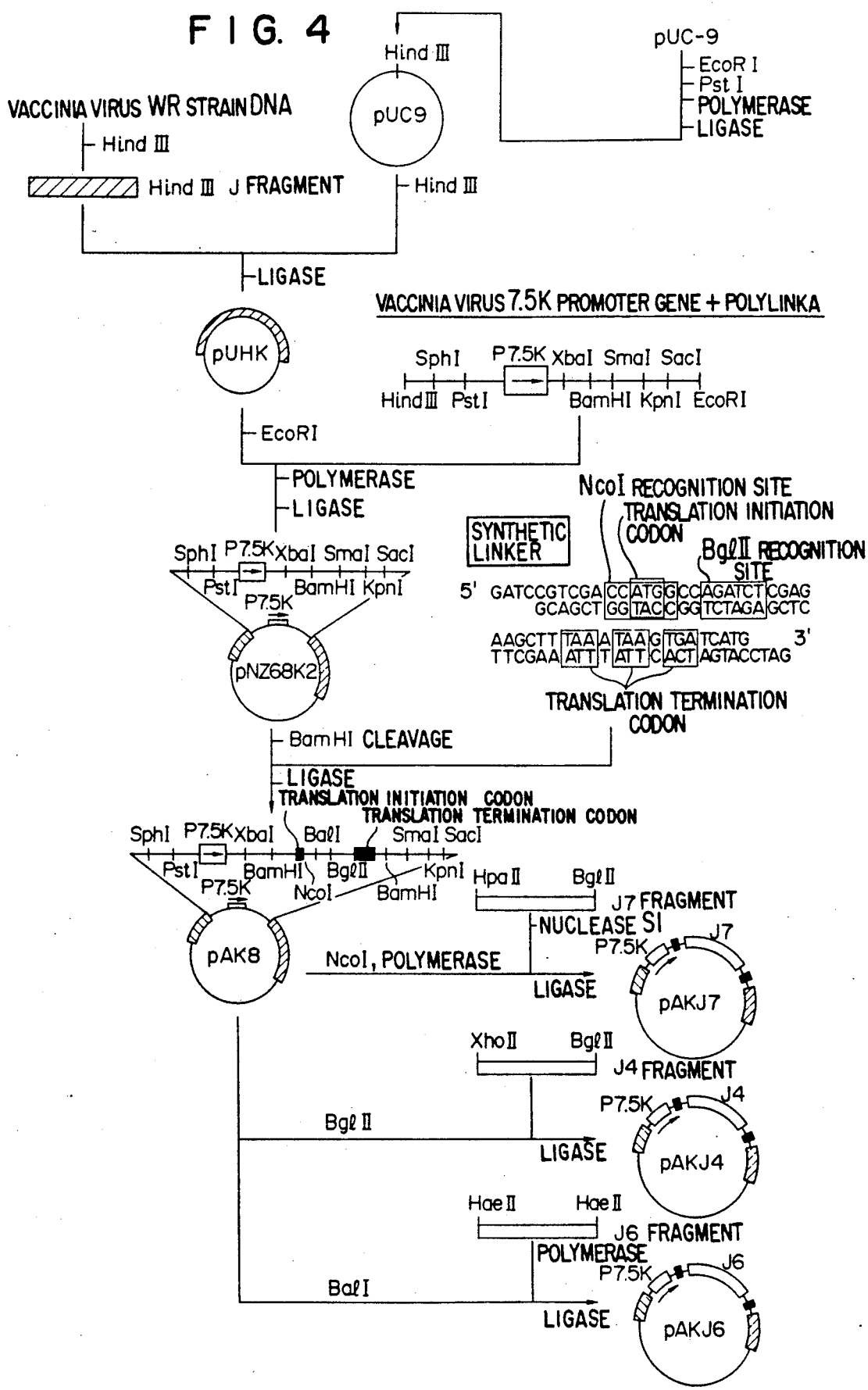
FIG. 4 shows procedures for constructing recombinant plasmid pAKJ4 containing E-protein-coding cDNA.

The virus used for constructing the recombinant virus in the present invention may be any virus classified into a vaccinia virus. Examples of such a virus include WR strain (Journal of Virology, 49, 857 (1984), Lister strain, temperature-sensitive mutant of Lister strain (cf., U.S. Pat. No. 4,567,147 and Japanese Patent Application KOKAI (Laid-Open) No. 44178/87), New York Board of Health strain, smallpox vaccine strains ("Vaccinia Viruses as Vectors for Vaccine Antigens", pp. 87-100, edited by J. Quinnan, Amsterdam, New York & Oxford, Elsevier Publishing Co.) such as LC16m8 strain and the like.

Among these viruses, preferred are those having a pock size on the chorioallantoic membrane of an embryonated egg of 3 mm or less and a shut-off temperature in rabbit kidney cells of 41° C. or lower. Specific examples are attenuated smallpox strains, LA and LB (CNTM-I-423) described in Japanese Patent Application KOKAI No. 44178/87 and LC16m8 strain described above.

These strains are extremely weakly toxic. Where the recombinant virus of the present invention is utilized as a live vaccine, the strains are advantageous in view of safety.

Furthermore, cDNA coding for a surface antigen protein of Japanese encephalitis virus can be constructed using, for example, the strain of Nakayama Health Institute described above, JaOAr strain (Arboviruses Research Institute Center, Eire University) or Sagayama strain (same center).

cDNA coding for E-protein constructed from, e.g., the aforesaid Sagayama strain is composed of 1500 base pairs in total as shown in FIG. 3. In the present invention, cDNA may be modified cDNA (namely, cDNA in which the base sequence is substituted, inserted or deleted) insofar as it has substantially the same function as in the aforesaid cDNA. The cDNA may also be modified to such an extent that amino acid sequences are different from each other, of course, as far as it has substantially the same function.

In practice of the present invention, there is constructed a first recombinant vector in which a DNA region non-essential to growth of vaccinia virus has been inserted. In this case, it is preferred to insert a promoter functioning in vaccinia virus into the region described above and further insert, at the downstream of the promoter, a translation initiation codon and a translation termination codon as well as a synthetic linker having a suitable restriction enzyme cleavage site between both.

The DNA region non-essential to growth as used herein refers to any non-essential DNA region that does not substantially affect growability of viruses, even though the region undergoes variation due to the insertion of heterogenous DNAs, for example, thymidine kinase (TK) gene or hemagglutinin (HA) gene of vaccinia virus, Hind III-cleaved F-fragment, M-fragment or N-fragment of vaccinia virus WR strain DNA (Virus, 36 (1), 23–33 (1986)), etc.

The promoter which functions in a vaccinia virus as used herein refers to a promoter having any base sequence as long as it can effectively function as a promoter in the transcription system possessed by a vaccinia virus, irrespective of synthetic or naturally occurring one. Specific examples include promoters found in a vaccinia virus described in, for example, Journal of Virology, 662–669 (1984); specifically, a promoter of vaccinia virus gene coding for 7.5K polypeptide, a promoter of vaccinia virus gene coding for 19K polypeptide, a promoter of vaccinia virus gene coding for 42K polypeptide, a promoter of vaccinia virus gene coding for thymidine kinase, a promoter of vaccinia virus gene coding for 28K polypeptide, a promoter of vaccinia virus gene coding for 11K polypeptide, etc.

A first recombinant vector can be constructed in a conventional manner; for example, after inserting a DNA fragment non-essential to the growth of vaccinia viruses into an appropriate vector (Japanese Patent Application KOKAI (Laid-Open) No. 129971/83, Japanese Patent Application KOHYO (Disclosure) No. 500518/85, Patent Application KOHYO (Disclosure) No. 44178/87, etc.). For example, after inserting a DNA fragment non-essential to growth of a vaccinia virus into an appropriate vector, a promoter to which a restriction enzyme cleavage sequence is added may be inserted, if necessary and desired, utilizing a restriction enzyme cleavage site present in the fragment.

Now, the protein of Japanese encephalitis virus is, after monocistronic synthesis, processed to divide into surface antigen proteins, etc., as described above. Accordingly, where cDNA to the whole virus genome is inserted, there is no necessity of artificially inserting a translation initiation codon and a translation termination codon; however, where only cDNA coding for E-protein is wished to be inserted, it is necessary that a translation initiation codon, a translation termination codon and a synthetic linker having a restriction enzyme cleavage sequence between both be inserted, utilizing a restriction enzyme cleavage site present at the downstream of the previously inserted promoter.

It is desired that the translation termination codon to be inserted be provided at 3 portions with a difference in reading frames so as to coincide therewith, even though E-protein-coding cDNA may take any of the reading frames.

cDNA to be inserted may be one containing genes also coding for other additional proteins, as long as it contains a region coding for E-protein. With respect to the virus belonging to the genus Flavivirus, regions coding for a matrix protein (hereafter referred to as M-protein), a prematrix protein (hereafter referred to as PreM-protein) and a core protein (hereafter referred to as C-protein) are present at the upstream of the region coding for E-protein. In the present invention, there may also be used a virus in which all or a part of cDNAs coding for these proteins may be linked to the E-protein-coding cDNA at the upstream thereof.

Specific examples of the vector used include plasmids such as pBR 322, pBR 325, pBR 327, pBR 328, pUC 7, pUC 8, pUC 9, pUC 19 and the like; phages such as λ phage, M 13 phage and the like; cosmids such as pHC 79 (Gene, 11, 291, 1980).

In the present invention, the region coding for E-protein of Japanese encephalitis virus is then inserted downstream of the promoter of a first recombinant vector thereby to construct a second recombinant vector. The method for insertion may also be performed in a conventional manner (e.g., cf. the patent publications supra). For example, a cDNA fragment derived from Japanese encephalitis virus may be inserted into the promoter of the first vector downstream thereof, utilizing a restriction enzyme cleavage site previously provided between the artificially added translation initiation codon and translation termination codon.

Upon construction of these first and second recombinant vectors, the *Escherichia coli* system which is easy in genetic manipulation may be used. Plasmid vectors to be used are not particularly limited as long as they are suited for purpose.

In the present invention, the second recombinant vector is then transfected to animal culture cells previously infected with a vaccinia virus to cause homologous recombination between the vector DNA and virus genome DNA, whereby a recombinant vaccinia virus is constructed.

The animal culture cell as used herein may be any cell insofar as a vaccinia virus can grow there. Specific examples include TK$^-$143 (derived from human osteosarcoma), FL (derived from human amnion), Hela (derived from carcinoma of human uterine cervix), KB (derived from carcinoma of human rhinopharynx), CV-1 (derived from monkey kidney), BSC-1 (derived from monkey kidney), RK13 (derived from rabbit kidney), L929 (derived from mouse connective tissue), CE (chicken embryo) cell, CEF (chicken embryo fibroblast), etc.

The construction of the recombinant vaccinia virus may be carried out in a conventional manner. According to, for example, DNA Cloning, Volume II, A Practical Approach, pp. 191–211, edited by D. M. Glover (IRL Press, Oxford, Wash.), the second recombinant vector treated by the calcium phosphate co-precipitation method is transfected into RK13 cells infected with a vaccinia virus; TK negative cells cultured on Eagle's MEM are infected with a mass of viruses containing the obtained recombinant virus; plaques grown in the presence of BUdR are selected as candidate strains for a recombinant virus. As a method for selecting a virus having inserted therein a DNA fragment coding for E-protein of Japanese encephalitis virus from these candidate strains, plaques are purified by hybridization using the DNA as a probe. Alternatively, immunoassay using anti-serum or monoclonal antibody may be utilized.

According to the present invention, there is thus obtained the recombinant vaccinia virus usable as live vaccine in which the cDNA coding for E-protein derived from Japanese encephalitis virus is inserted into the genome region non-essential to growth of a vaccinia virus, together with the DNA having a promoter function, in a form capable of expression.

EXAMPLES

The present invention will be described in more detail with reference to the examples below.

EXAMPLE 1

(1) Extraction of RNA genome from Japanese encephalitis virus

Mosquito-derived established cell C6/36 (J. Gen. Virol., 40, 531-544 (1978)) was infected with Japanese encephalitis virus Sagayama strain. After growing the virus, the culture supernatant was mixed with polyethylene glycol. The mixture was centrifuged to purify Japanese encephalitis virus. After extraction from the purified virus with phenol, ethanol was added to the extract to cause precipitation, whereby virus genome RNA (about 11 Kbp) was isolated.

(2) Cloning of Japanese encephalitis virus cDNA (cf. FIG. 1)

Using poly(A) polymerase (Takara Shuzo Co., Ltd.), poly(A) was added to the virus genome RNA prepared in (1). Using the same as a template, 4 kinds (A, G, C, T) of deoxyribonucleoside triphosphates and reverse transcriptase were acted using oligo dT as a primer to synthesize first strand cDNA. Next, double stranded cDNA was constructed using E. coli RNase H and 4 kinds (A, G, C, T) of deoxyribonucleoside triphosphates and E. coli DNA polymerase (Molecular Cloning [Cold Spring Harbor Lab., (1982)], p. 211-246) and, dC chain was added using terminal transferase. On the other hand, after digesting plasmid pUC 9 (manufactured by Pharmacia) with restriction enzyme Pst I, dG chain was added to the digestion product by terminal transferase. The dG chain-added product was mixed with the cDNA described above. The mixture was subjected to ligation to cyclize. This recombinant plasmid was introduced into E. coli HB 101 competent cell to obtain a transformant. A plasmid was taken out from the transformant and length of insert cDNA was compared on agarose gel. With respect to the longest insert cDNA, a sequence at the 5'-side was analyzed (Gene, 19, 269 (1982)). Based on the results of sequential analysis, cDNA was again constructed by the method described above using 20-mer synthetic oligonucleotide (5'-dATTCCGTACCATGCAGTCCA-3') as a primer and virus genome RNA as a template. The cDNA was ligated with plasmid pUC 9 to obtain a number of transformants. From the obtained transformants, a transformant containing a recombinant plasmid bearing cDNA coding for the objective surface antigen protein was selected by a method described below.

With respect to a method for constructing cDNA clone of Japanese encephalitis virus, an example of constructing cDNA clone using Japanese encephalitis virus JaOArS 982 strain in a similar manner is described in Gene, 48, 195-201 (1986).

(3) Screening of recombinant plasmid pJE 4118 containing cDNA (4118) coding for surface antigen protein of Japanese encephalitis virus (cf. FIGS. 1 and 2)

The transformants obtained in (2) were replicated onto a nitrocellulose filter. After gently washing the replicated filter with 0.2% NP-40 (surfactant, Nakarai Kagaku), the filter was subjected to immunoscreening using anti-JE serum. One transformant capable of positively reacting was obtained, while the reactivity was weak. A plasmid possessed by the strain was named pJE 4118. Then, plasmid pJE 4118 was prepared in a conventional manner (Molecular Cloning, 75-95, [supra]) and cDNA inserted into plasmid pUC 9 was excised with restriction enzyme Pst I. Using this cDNA as a DNA probe, the various transformants obtained in (2) were subjected to screening by the colony hybridization method (Molecular Cloning, 382-387 [supra]). A plasmid bearing cDNA overlapping with the insert cDNA (4118) of pJE 4118 was selected. The thus seleced cDNA(2-20) was recovered from plasmid and its positional relationship was determined by restriction enzymes (cf. FIG. 2). It was thus made clear that cDNA (2-20) partially overlapped with the N-end of Japanese encephalitis virus (4118).

(4) Analysis of a base sequence of cDNA coding for surface antigen protein (cf. FIG. 3)

Recombinant plasmids pJE 4118 and pJE 2-20 were cleaved with restriction enzyme Pst I to give DNA fragments of about 2.5 Kbp and about 1.0 Kbp, respectively. With respect to these fragments, their sequences were analyzed by the method of Messing et al. using M 13 phage (Gene, 19, 269 (1982), Science, 241, 1205 (1981), from the 5'-end in the case of cDNA (4118) and from the 3'-end in the case of cDNA (2-20).

As a result, it has been noted that a cDNA sequence at portions where both were overlapping was 334 bases from the third codon of the 5th amino acid to the 116th amino acid in FIG. 3. Based on comparison of an amino acid sequence expected from this base sequence with an amino acid sequence of E-protein of yellow fever virus (akin to and belonging to the same genus as in Japanese encephalitis virus) already known (Science, 229, 726-733 (1985)), it has been deduced that E-protein of Japanese encephalitis virus is amino acids from +1st to the 500th shown in FIG. 3.

Likewise, it has been deduced that M-protein of Japanese encephalitis virus is amino acids from the −75th to the −1st and, PreM-protein is amino acids from the −167th to the −76th as shown in FIG. 3. Furthermore, it has been deduced that the 5'-end of PreM-protein codes for a part of C-protein of Japanese encephalitis virus.

(5) Construction of cDNA coding for Japanese encephalitis virus constituent protein (cf. FIGS. 2 and 3)

cDNA (4118) is deleted of 5 amino acids at the N-end of E-protein. Thus, splicing was made at the Aat II site using cDNA (2-20) to obtain cDNA (203) fully covering E-protein.

(a) A fragment of about 1.6 Kbp obtained by preparing Hpa II-Hpa I fragment (about 810 bp) and Hpa I-Bg§ II fragment (about 800 bp) from cDNA fragment (J7): cDNA (203) and ligating them. This fragment scarcely contains a region encoding M-protein present at the upstream of a region coding for E-protein. NS1 in FIG. 2 means a region coding for non-constituent protein.

(b) A fragment of about 2.1 Kbp obtained by treating cDNA fragment (J4): cDNA (203) with Xho II and Bg§ II. This fragment contains a region encoding M-protein, in addition to a region coding for E-protein.

(c) A fragment of about 2.4 Kbp obtained by treating cDNA fragment (J6): cDNA (203) with Hae II. This fragment contains E-protein, M-protein, PreM-protein and a part of C-protein.

(6) Construction of a first recombinant vector pAK 8 containing vaccinia virus TK gene having inserted therein polylinker and vaccinia virus 7.5K promoter (cf. FIG. 4)

After digesting pUC 9 with EcoR I and Pst I, the digestion product was treated with polymerase, where the cleaved end was blunted and ligated to construct pUC 9 deleted of EcoR I site. After cleaving this EcoR I site-deleted pUC 9 with Hind III, the cleaved product was ligated with Hind III J fragment of vaccinia virus Wr strain to obtain recombinant vector pUHK. Then, after 7.5K promoter of vaccinia virus Wr strain (Moss et al., Cell, 125, 805–813, 1981) was inserted into Hinc II site of pUC 19 (manufactured by Pharmacia), cleavage was preformed in sequence with Hind III and EcoR I to give a DNA fragment (about 350 bp) having a polylinker before and after the 7.5K promoter.

After the DNA fragment (cf. FIG. 4) and the EcoR I digestion product of plasmid pUHK described above were treated with polymerase, ligation was performed. The obtained recombinant plasmid was named pNZ68K2.

Then, a synthetic linker having BamH I site at both ends thereof which had a translation initiation codon, a translation termination codon and a restriction enzyme cleavage sequence (Bg§ II, Nco I) between both was synthesized (cf. FIG. 4) and inserted into BamH I site of pNZ68K2 to construct the objective first recombinant plasmid pAK8.

(7) Construction of a second recombinant plasmid having inserted DNA coding for surface antigen protein of Japanese encephalitis virus at the downstream of 7.5K promoter (cf. FIG. 4)

(a) Construction of a second recombinant plasmid (pAKJ7) having inserted cDNA (J7) therein After treating cDNA (J7) obtained in (5) with nuclease S1, the product was ligated with cleaved plasmid obtained by digesting plasmid pAK8 obtained in (6) with Nco I and then treating with polymerase. Thus recombinant plasmid pAKJ7 having inserted cDNA (J7) at the downstream of 7.5K promoter and between the translation initiation codon and the translation termination codon was obtained.

This plasmid is selected as forming about 0.4 Kbp DNA fragment when cleaved with restriction enzyme Nco I. For information, in the case of a recombinant plasmid having inserted cDNA (J7) in the reversed direction, a DNA fragment of about 1.2 Kbp is formed.

(b) Construction of a second recombinant plasmid (pAKJ4) having inserted cDNA (J4) therein cDNA (J4) obtained in (5) was ligated with the digestion product of plasmid pAK8 obtained in (6) with Bg§ II to obtain recombinant plasmid pAKJ4 having inserted cDNA (J4) at the downstream of 7.5K promoter and between the translation initiation codon and the translation termination codon.

This plasmid was selected as forming about 0.74 Kbp DNA fragment when cleaved with restriction enzyme Nco I.

(c) Construction of a second recombinant plasmid (pAKJ6) having inserted cDNA (J6) therein After treating cDNA (J6) obtained in (5) with polymerase, the product was ligated with the digestion product of plasmid pAK8 obtained in (6) with Bal I to obtain recombinant plasmid pAKJ6 having inserted cDNA (J6) at the downstream of 7.5K promoter and between the translation initiation codon and the translation termination codon.

This plasmid was selected as forming about 0.4 Kbp DNA fragment and about 0.7 Kbp DNA fragment when cleaved with restriction enzyme Nco I.

(8) Preparation of a recombinant vaccinia virus

Attenuated smallpox virus strain (attenuated smallpox virus LA strain described in Japanese Patent Application KOKAI (Laid-Open) No. 44178/87, a shut-off temperature in rabbit kidney cells of 41° C., a pock size on the chorioallantoic membrane of an embryonated egg of 2–3 mm) cultured in a culture bottle of 25 cm$^2$ was inoculated in 0.1 pfu/cell. Forty-five minutes after, 10 μg each of various recombinant plasmids obtained in (7) (pAKJ7, pAKJ4, pAKJ6) was dissolved in 2.2 ml of sterilized water and, DNA-calcium phosphate co-precipitates were prepared by the method of Hidaka et al. (Protein, Nucleic Acid and Enzyme, 27, 340, 1985). Then, 0.5 ml of the co-precipitates was dropwise added onto the infected RK-13 cells. After settling in a 7% CO$_2$ incubator at 37° C. for 30 minutes, 4.5 ml of Eagle's MEM containing 5% bovine fetal serum was added thereto. Three hours after the addition, the culture solution was exchanged followed by culturing at 37° C. in 7% CO$_2$ incubator for 48 hours. The system including the culture cells was frozen and melted 3 times.

For selection of a recombinant, the virus solution described above was inoculated on TK$^-$143 cells cultured in a Petri dish of 10 cm. Thirty minutes after, Eagle's MEM supplemented with 1% agarose, 5% bovine fetal serum and 25 μg/ml BUdR was overlaid thereon in layers. After culturing for 3 days, the infected cells were stained with 0.01% neutral red. From the formed plaque, virus was withdrawn with a Pasteur pipette and suspended in PBS containing 2% gelatin. In order to perform dot hybridization, a part of the suspension was spotted onto nylon or nitrocellulose membrane and the balance was stored at −20° C. After repeating a treatment with 0.5N NaOH for 10 minutes and with 1M Tris-hydrochloride buffer for 5 minutes 3 times, the spotted membrane was treated with 1.5M NaCl and 0.5M Tris-hydrochloride buffer for 5 minutes. Saturation was effected with 2-fold SSC (1-fold SSC, 0.15M NaCl, 0.015M sodium citrate) and sintered at 80° C. for 2 hours. The system was treated with 4-fold SET (0.6M NaCl, 0.08M Tris HCl, 4 mM EDTA (pH 7.8))-10-fold Denhardt-0.1% SDS at 68° C. for 2 hours. 4-Fold SET- 10-fold Denhardt-0.1% SDS-0.1% Na$_4$P$_2$O$_7$-50 μg/ml-modified salmon sperm DNA and Japanese encephalitis virus E-protein cDNA labeled with $^{32}$P were hybridized by nick translation at 68° C. for 14 hours. After washing, the membrane was put on an X ray film, which was subjected to autoradiography and a blackened spot on the film was selected. The virus solution corresponding to the blackened spot was again inoculated on TK$^-$143 cells. Thirty minutes after, Eagle's MEM supplemented with 1% agarose, 5% bovine fetal serum and 25 μg/ml Bud R was overlaid thereon in layers. After culturing for 3 days, the infected cells were stained with 0.01% neutral red. With respect to the formed plaque, procedures were performed in a manner similar to the above. The purification procedures were repeated until the appearing plaques were all blackened by dot hybridization. The thus obtained viruses were objective recombinant vaccinia viruses, which were named LAJ7, LAJ4 and LAJ6, respectively, corresponding to the recombinant plasmids used.

(9) Expression of recombinant vaccinia virus in infected cells (a) Determination by anti-V3 antibody The recombinant virus strain of the present invention showing m.o.i of 1.0 or 0.1 were inoculated on RK 13 cells cultured in a chamber slide for tissue culture. After infecting at 37° C. for an hour, the virus solution was withdrawn and the cells were washed with MEM. Then Eagle's MEM containing 5% bovine fetal serum was added thereto. Sixteen minutes after, Eagle's MEM was withdrawn and gently washed PBS (phosphate buffered saline) followed by air drying. The cells were treated with acetone at room temperature for 5 minutes to immobilize the cells. Examination was made by indirect fluorescent antibody technique using as a primary antibody anti-V3 antibody and as a secondary antibody fluorescein isocyanate-bound anti-rabbit IgG antibody. As a result, it was confirmed that the 3 recombinant vaccinia viruses had Japanese encephalitis virus E-protein productivity. A method for preparing anti-V3 antibody is as follows.

Japanese encephalitis virus was decomposed in PBS containing 1% SDS and 0.1% 2-mercaptoethanol. E-protein was isolated by 10% polyacrylamide gel electrophoresis. The gel was excised to recover E-protein. The thus obtained E-protein was inoculated in rabbit to recover anti-V3 antibody. The thus obtained anti-V3 antibody recognizes and reacts with modified E-protein, namely, a primary structure of protein.

(b) Determination by anti-JEV antibody

A positive or negative production of E-protein having a biological activity was examined in a manner similar to the above except for using anti-JEV antibody (anti-serum prepared by inoculating Japanese encephalitis virus itself) as a primary antibody.

This anti-JEV antibody was prepared based on Japanese encephalitis virus having biological activities so that protein capable of reacting with anti-JEV antibody is present on the surface of Japanese encephalitis virus. It is assumed that anti-JEV antibody would have activities similar to protein having biological activities.

The results are summarized in Table 2. From the results, it is shown that any recombinant virus produces E-protein; especially E-protein LAJ6 produced had biological activities similar to those of E-protein present on the surface of Japanese encephalitis virus.

TABLE 2

| Vaccinia Virus Strain | Primary Antibody | | |
|---|---|---|---|
| | Anti-V3 Antibody | Anti-JEV Antibody | Anti-vaccinia Antibody |
| LA (parent strain) | − | − | +++ |
| LAJ7 | ++ | − | +++ |
| LAJ4 | ++ | ± | +++ |
| LAJ6 | +++ | ++ | +++ |

− not responsive
± impossible to determine
+ weak response
++ strong response
+++ extremely strong response

What is claimed is:

1. A recombinant vaccinia virus having inserted cDNA coding for a surface antigen protein of Japanese encephalitis virus containing a cDNA coding for a whole or substantially all of prematrix protein of Japanese encephalitis virus, a cDNA containing a whole or substantially all of cDNA coding for matrix protein of Japanese encephalitis virus and a cDNA containing the whole or a substantially all of E-protein of Japanese encephalitis virus in sequence, respectively, into a genome region non-essential to growth of a vaccinia virus, wherein said cDNA coding for said surface antigen is of sufficient length to code for a protein having improved antigenic properties as compared with said E-protein.

2. A recombinant vaccinia virus as claimed in claim 1, wherein said cDNA is under control of a promoter.

3. A recombinant vaccinia virus as claimed in claim 1 or 2, wherein said cDNA incorporated is inserted between a synthesized translation initiation codon and translation termination codon.

4. A recombinant vaccinia virus as claimed in claim 1 or 2, wherein said cDNA coding for surface antigen protein of Japanese encephalitis virus encodes an amino acid sequence of FIG. 3 or polypeptide having substantially the same function as the amino acid sequence.

5. A recombinant vaccinia virus as claimed in claim 1, which contains the whole cDNA coding for matrix protein of Japanese encephalitis virus.

6. A recombinant vaccinia virus having inserted therein a whole or substantially all of cDNA coding for prematrix protein of Japanese encephalitis virus, a whole or substantially all of cDNA coding for matrix protein of Japanese encephalitis virus and a whole or substantially all of cDNA coding for E-protein of Japanese encephalitis virus in sequence, respectively, into a genome region non-essential to growth of a vaccinia virus wherein said cDNAs are inserted between a synthesized translation initiation codon and a translation termination codon and wherein said cDNA is under control of a promoter.

7. A recombinant vaccinia virus as claimed in claim 6, containing a whole or substantially all of the cDNA sequence set forth in FIG. 3 beginning at position −167 and continuing to position +500.

8. A recombinant vaccinia virus as claimed in claim 7, which further comprises a part of the cDNA coding for C-Protein of Japanese encephalitis virus at the 5′ end of said cDNA sequence.

* * * * *